United States Patent
Minagawa et al.

(10) Patent No.: US 10,092,680 B2
(45) Date of Patent: Oct. 9, 2018

(54) METAL MEDICAL DEVICE

(71) Applicant: SUMITOMO RUBBER INDUSTRIES, LTD., Kobe-shi, Hyogo (JP)

(72) Inventors: Yasuhisa Minagawa, Kobe (JP); Takefumi Nakashita, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 112 days.

(21) Appl. No.: 14/828,697

(22) Filed: Aug. 18, 2015

(65) Prior Publication Data

US 2016/0058919 A1 Mar. 3, 2016

(30) Foreign Application Priority Data

Sep. 2, 2014 (JP) .................. 2014-178433

(51) Int. Cl.
*A61L 31/02* (2006.01)
*A61L 31/10* (2006.01)

(52) U.S. Cl.
CPC ............. *A61L 31/10* (2013.01); *A61L 31/022* (2013.01); *A61L 2400/10* (2013.01)

(58) Field of Classification Search
CPC .... A61L 31/10; A61L 2400/10; A61L 31/022; C08L 83/04
See application file for complete search history.

(56) References Cited

U.S. PATENT DOCUMENTS

| | | | |
|---|---|---|---|
| 5,443,511 A | 8/1995 | Ogawa et al. | |
| 5,688,747 A | 11/1997 | Khan et al. | |
| 5,954,869 A | 9/1999 | Elfersy et al. | |
| 6,458,867 B1 * | 10/2002 | Wang ..................... | A61L 29/085 523/105 |
| 6,599,558 B1 | 7/2003 | Al-Lamee et al. | |
| 7,160,592 B2 * | 1/2007 | Rypacek ................ | A61L 31/10 424/422 |
| 2007/0048349 A1 * | 3/2007 | Salamone ............... | A61L 27/34 424/423 |
| 2009/0280157 A1 * | 11/2009 | Maas ..................... | C08F 265/00 424/426 |
| 2009/0317443 A1 | 12/2009 | Willis et al. | |
| 2010/0076546 A1 * | 3/2010 | Dias ........................ | A61L 29/10 623/1.46 |
| 2011/0086234 A1 | 4/2011 | Stasko et al. | |

FOREIGN PATENT DOCUMENTS

| | | |
|---|---|---|
| CN | 1635915 A | 7/2005 |
| CN | 102782056 A | 11/2012 |
| CN | 103193927 A | 7/2013 |
| EP | 0810239 A2 * | 12/1997 |
| JP | 4-250158 A | 9/1992 |
| JP | 5-115541 A | 5/1993 |
| JP | 7-47120 A | 2/1995 |
| JP | 7-289630 A | 11/1995 |
| JP | 10-231 A | 1/1998 |
| JP | 10-330383 A | 12/1998 |
| JP | 2001-29452 A | 2/2001 |
| JP | 2002-502286 A | 1/2002 |
| JP | 2003-520107 A | 7/2003 |
| JP | 2006-061273 A | 3/2006 |
| JP | 2007-196211 A | 8/2007 |
| JP | 6034506 B2 | 11/2016 |
| WO | WO 01/52915 A1 | 7/2001 |
| WO | WO 01/60923 A1 | 8/2001 |
| WO | WO 03/022322 A2 | 3/2003 |
| WO | WO 2008/023604 A1 | 2/2008 |
| WO | 2009/012353 A2 * | 1/2009 |
| WO | 2009009628 A2 * | 1/2009 |
| WO | 2009/085817 A1 * | 7/2009 |
| WO | WO 2011/047013 A1 | 4/2011 |
| WO | WO 2011/076924 A1 | 6/2011 |
| WO | WO 2013/016849 A1 | 2/2013 |

OTHER PUBLICATIONS

Chin-Quee et al., "Endothelial Cell Recovery, Acute Thrombogenicity, and Monocyte Adhesion and Activation on Fluorinated Copolymer and Phosphorylcholine Polymer Stent Coatings," Biomaterials, vol. 31, 2010 (published online Oct. 12, 2009), pp. 648-657.
Arkles, "Hydrophobicity, Hydrophilicity and Silane Surface Modification", Gelest, Self-Assembled Monolayers (SAMs), Version 2.0, 2011, pp. 1-80 (84 pages total), XP-55098863.
International Search Report, issued in PCT/JP2014/076887, dated Dec. 22, 2014.
Partial English translation of Chinese Office Action for Chinese Application No. 201480054969.5, dated May 2, 2018.
Written Opinion of the International Searching Authority, issued in PCT/JP2014/076887(PCT/ISA/237), dated Dec. 22, 2014.
Xue et al., "Surface Modification and Physical Property Study of Inorganic Nanomaterials," 1st Edition, Hefei Industrial University Press, Oct. 31, 2009, pp. 122-123 (4 pages total).

* cited by examiner

*Primary Examiner* — Alma Pipic
(74) *Attorney, Agent, or Firm* — Birch, Stewart, Kolasch & Birch LLP

(57) ABSTRACT

The present invention provides metal medical devices which are provided with sliding properties (lubricity), low protein adsorption properties and low cell adsorption properties and further in which these properties are prevented from deteriorating. The present invention relates to a metal medical device having a surface at least partially treated with a copolymer C of a polymerizable silane compound A and a polymerizable compound B that contains a functional group.

6 Claims, No Drawings

METAL MEDICAL DEVICE

TECHNICAL FIELD

The present invention relates to metal medical devices.

BACKGROUND ART

Guide wires, stents, and the like are inserted into and optionally placed in blood vessels, respiratory tracts, urethra, and other body cavities or tissues in some cases. When such a medical device as guide wires and stents is inserted into the body, the medical device may damage the tissue or the like in the body and produce inflammation or cause pain to the patient. To ameliorate these problems, it has been necessary to improve the sliding properties of the medical devices to be inserted into the body.

Moreover, stents and the like which are placed in the body for a long period of time are required to be prevented, as far as possible, from adsorbing proteins and cells on their surface because the adsorption of proteins and cells on the surface can lead to problems such as the formation of a blood clot clogging a blood vessel.

To ameliorate the above problems, a method has been proposed in which the surface of a medical device such as guide wires and stents is coated with a hydrophilic resin, a fluororesin or the like.

SUMMARY OF INVENTION

Technical Problem

As described above, various methods have been tried to impart lubricity to the surface of medical devices to improve the sliding properties thereof. However, all the methods only allow the surface of medical devices to be coated with a resin or to be cured after the coating. Especially in the case where the surface of the medical device is made of a metal, since the coating resin is not firmly bonded to the surface of the medical device, it can be easily peeled or removed from the surface of the medical device, with the result that unfortunately the sliding properties of the medical device are deteriorated. Another problem is that proteins and cells gradually adhere to the surface of the indwelling medical device. Accordingly, the development of metal medical devices in which deterioration of sliding properties and deterioration of low protein and cell adsorption/adhesion abilities are prevented has been desired.

The present invention aims to solve the above problems and provide metal medical devices which are provided with sliding properties (lubricity), low protein adsorption properties and low cell adsorption properties and further in which these properties are prevented from deteriorating.

Solution to Problem

The present invention relates to a metal medical device, having a surface at least partially treated with a copolymer C of a polymerizable silane compound A and a polymerizable compound B that contains a functional group.

The present invention also relates to a metal medical device, having a surface at least partially treated with a polymer e, the polymer e being obtained by reacting a copolymer c with a silane compound d, the copolymer c being formed from a polymerizable compound a that is reactive with the silane compound d, and a polymerizable compound b that contains a functional group.

The functional group is preferably a polyoxyalkylene group, a metal salt-containing hydrophilic group, a halide salt-containing hydrophilic group, a zwitterionic group, or a fluorine-containing hydrophobic group.

The metal salt-containing hydrophilic group is preferably an alkali metal salt-containing hydrophilic group or an alkaline earth metal salt-containing hydrophilic group.

The halide salt-containing hydrophilic group is preferably a chlorine salt-containing hydrophilic group.

The zwitterionic group is preferably a betaine group.

The fluorine-containing hydrophobic group is preferably a perfluorooxyalkylene group.

Advantageous Effects of Invention

Since the metal medical devices of the present invention have a surface treated with a specific polymer, sliding properties (lubricity), low protein adsorption properties and low cell adsorption properties are imparted to the surface of the metal medical devices, and further deterioration of these properties can be prevented.

DESCRIPTION OF EMBODIMENTS

The present invention relates to (1) a metal medical device having a surface at least partially treated with a copolymer C of a polymerizable silane compound A and a polymerizable compound B that contains a functional group, and (2) a metal medical device having a surface at least partially treated with a polymer e, wherein the polymer e is obtained by reacting a copolymer c with a silane compound d, and the copolymer c is formed from a polymerizable compound a that is reactive with the silane compound d, and a polymerizable compound b that contains a functional group.

Lubricant layers on the surfaces of metal medical devices formed by conventional surface treatment or coating methods are easily peeled or removed by a stress such as rubbing by a hand, and are therefore disadvantageous in terms of maintaining sliding properties (lubricity), low protein adsorption properties and low cell adsorption properties. In contrast, in the metal medical devices of the present invention, the surface treatment with the copolymer C or polymer e causes a dehydration/deoxygenation condensation reaction between hydroxy groups present on the surface of the metal medical device and the moiety derived from the silane compound A or d of the copolymer C or polymer e, thereby forming a chemical bond which prevents peeling or removal of the lubricant layer. Thus, good sliding properties (lubricity), low protein adsorption properties and low cell adsorption properties are imparted and, further, deterioration of these properties can be prevented.

In particular, when the functional group of the polymerizable compound B used is a polyoxyalkylene group, a metal salt-containing hydrophilic group, a halide salt-containing hydrophilic group, or a zwitterionic group, the sliding properties is more significantly improved because these groups are so highly compatible with water that more water molecules are held around them and provide fluid lubrication.

When the functional group is a fluorine-containing hydrophobic group, on the other hand, the surface tension is significantly lowered and, accordingly, the force of molecular adhesion between the surface of the metal medical device and an object contacting the surface (for example, the inner surface of a catheter, somatic cells or the like when the metal medical device is a guide wire) is greatly reduced, so that sliding properties are more greatly improved.

Furthermore, the lubricant layer is prevented from being washed away and removed during the long indwelling time and, therefore, deterioration of low protein adsorption and low cell adsorption properties is prevented.

The metal medical devices of the present invention have a surface treated with the copolymer C or polymer e at least at a portion where lubricity, low protein adsorption properties and low cell adsorption properties are required. The entire surface of the metal medical devices may be treated with the copolymer C or polymer e.

The copolymer C is obtained by copolymerization of a polymerizable silane compound A and a polymerizable compound B that contains a functional group.

The polymerizable silane compound A may be, for example, a silane compound having at least one polymerizable group in the molecule. Examples of the polymerizable group include a (meth)acrylic group, an allyl group, a vinyl group, and a styryl group. Particularly preferred is a (meth) acrylic group.

In view of the effect of the present invention, the silane compound A is preferably a compound represented by the following Formula (1):

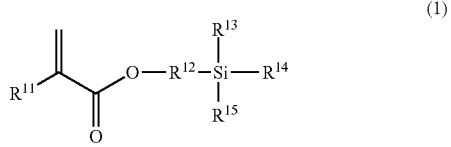

(1)

wherein $R^{11}$ represents a hydrogen atom or a linear or branched C1-C3 alkyl group; $R^{12}$ represents a linear or branched C1-C5 alkylene group; and $R^{13}$ to $R^{15}$ are the same as or different from one another and each represent a halogen atom, a hydroxy group, a linear or branched C1-C3 alkyl group, or a linear or branched C1-C3 alkoxy group, provided that at least one of $R^{13}$ to $R^{15}$ is a halogen atom, a hydroxy group, or a linear or branched C1-C3 alkoxy group.

In Formula (1), $R^{11}$ is a hydrogen atom or a linear or branched C1-C3 alkyl group, and is preferably a hydrogen atom or a linear or branched C1-C2 alkyl group. Specific examples include a hydrogen atom, a methyl group, an ethyl group, a propyl group, and an isopropyl group. Preferred are a hydrogen atom, a methyl group, and an ethyl group, and more preferred are a hydrogen atom and a methyl group.

In Formula (1), $R^{12}$ is a linear or branched C1-C5 alkylene group, and is preferably a linear or branched C1-C3 alkylene group. Specific examples include a methylene group, an ethylene group, a propylene group, an isopropylene group, and a butylene group. Preferred are a methylene group, an ethylene group, and a propylene group.

In Formula (1), $R^{13}$ to $R^{15}$ are the same as or different from one another and each represent a halogen atom, a hydroxy group, a linear or branched C1-C3 alkyl group, or a linear or branched C1-C3 alkoxy group. Specific examples include a fluorine atom, a chlorine atom, a bromine atom, a methyl group, an ethyl group, a propyl group, an isopropyl group, a methoxy group, an ethoxy group, a propoxy group, and an isopropoxy group. Here, at least one of $R^{13}$ to $R^{15}$ is a halogen atom, a hydroxy group, or a linear or branched C1-C3 alkoxy group, and is preferably a linear or branched C1-C3 alkoxy group.

Examples of the compound represented by Formula (1) include 3-(meth)acryloxypropyltrimethoxysilane, 3-(meth) acryloxyethyltrimethoxysilane, 3-(meth)acryloxymethyltrimethoxysilane, 3-(meth)acryloxypropyltriethoxysilane, 3-(meth)acryloxyethyltriethoxysilane, 3-(meth)acryloxymethyltriethoxysilane, 3-(meth)acryloxypropylmethyldimethoxysilane, 3-(meth)acryloxyethylmethyldimethoxysilane, 3-(meth)acryloxymethylmethyldimethoxysilane, 3-(meth) acryloxypropylmethyldiethoxysilane, 3-(meth)acryloxyethylmethyldiethoxysilane, 3-(meth)acryloxymethylmethyldiethoxysilane, 3-(meth)acryloxypropyldimethylethoxysilane, 3-(meth)acryloxyethyldimethylethoxysilane, 3-(meth)acryloxymethyldimethylethoxysilane, 3-(meth)acryloxypropyldimethylmethoxysilane, 3-(meth)acryloxyethyldimethylmethoxysilane, and 3-(meth) acryloxymethyldimethylmethoxysilane. Preferred among these are 3-(meth)acryloxypropyltrimethoxysilane and 3-(meth)acryloxypropyltriethoxysilane, and more preferably 3-(meth)acryloxypropyltrimethoxysilane, because the effect of the present invention can be better achieved.

The polymerizable compound B that contains a functional group may be, for example, a compound containing in the molecule at least one polymerizable group and a functional group imparting functional properties such as lubricity, low protein adsorption properties and low cell adsorption properties. Examples of the polymerizable group include those mentioned for the silane compound A, and preferred are those described for the preferred silane compound A. In view of imparting lubricity, low protein adsorption properties and low cell adsorption properties, the functional group is preferably a polyoxyalkylene group, a metal salt-containing hydrophilic group, a halide salt-containing hydrophilic group, a zwitterionic group, or a fluorine-containing hydrophobic group.

Examples of the polyoxyalkylene group include linear or branched groups represented by —(OR)$_n$— wherein R represents a C1-C4 alkylene group, and n represents an integer of 2 or higher (e.g., a polyoxyethylene group, a polyoxypropylene group), and the like.

The metal salt-containing hydrophilic group is not particularly limited as long as it is a group that contains a hydrophilic moiety corresponding to a metal salt. In view of water-holding properties, the metal salt is preferably a metal carboxylate, a phosphonate metal salt, or a metal sulfonate. In view of water-holding properties, the metal of the metal salt-containing hydrophilic group is preferably an alkali metal or an alkaline earth metal, and more preferably lithium, sodium, potassium, magnesium, or calcium.

The halide salt-containing hydrophilic group is not particularly limited as long as it is a group that contains a hydrophilic moiety corresponding to a halide salt. In view of water-holding properties, the halide salt is preferably an ammonium halide salt. Examples of the halogen of the halide salt-containing hydrophilic group include fluorine, chlorine, bromine, and iodine. In view of water-holding properties, preferred among these are chlorine and bromine, with chlorine being more preferred.

The zwitterionic group (a functional group bearing a center of permanent positive charge and a center of negative charge) is not particularly limited. Betaine groups such as carboxybetaine, sulfobetaine, and phosphobetaine groups are preferred in view of water-holding properties.

Examples of the fluorine-containing hydrophobic group include perfluoroether groups (perfluorooxyalkylene groups).

In view of the effect of the present invention, the polymerizable compound B that contains a functional group as mentioned above is suitably a compound containing a metal salt-containing hydrophilic group, a halide salt-containing hydrophilic group, or a zwitterionic group.

Specifically, the polymerizable compound B containing a metal salt-containing hydrophilic group is preferably a compound represented by the following Formula (2):

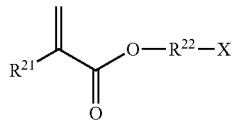

(2)

wherein $R^{21}$ represents a hydrogen atom or a linear or branched C1-C3 alkyl group; $R^{22}$ represents a linear or branched C1-C5 alkylene group; and X represents a metal salt-containing hydrophilic group.

In Formula (2), examples of $R^{21}$ include those mentioned for $R^{11}$ in Formula (1), and preferred are those described for the preferred $R^{11}$ in Formula (1). Examples of $R^{22}$ include those mentioned for $R^{12}$ in Formula (1), and preferred are those described for the preferred $R^{12}$ in Formula (1).

The metal salt-containing hydrophilic group designated by X in Formula (2) is preferably, for example, a functional group represented by any of the Formulae (2-1) to (2-3) below. Among these, it is more preferably a functional group represented by the Formula (2-3) because the effect of the present invention can be better achieved.

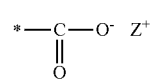

(2-1)

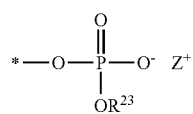

(2-2)

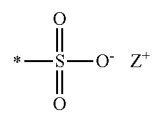

(2-3)

In Formula (2-2), $R^{23}$ represents a linear or branched C1-C3 alkyl group, and particularly preferably a methyl group, an ethyl group, or a propyl group. In Formulae (2-1) to (2-3), $Z^+$ represents a monovalent metal ion, and particularly preferably a sodium ion, a potassium ion, or a lithium ion. Moreover, in Formulae (2-1) to (2-3), * represents a bond.

Examples of the compound represented by Formula (2) include 3-sulfopropyl(meth)acrylate potassium salt, sulfomethyl(meth)acrylate potassium salt, 2-sulfoethyl(meth)acrylate potassium salt, 3-phosphopropyl(meth)acrylate potassium salt, 3-carboxypropyl(meth)acrylate potassium salt, 3-sulfopropyl(meth)acrylate sodium salt, and 3-sulfopropyl (meth)acrylate lithium salt. Preferred among these is 3-sulfopropyl(meth)acrylate potassium salt because the effect of the present invention can be better achieved.

Specifically, the polymerizable compound B containing a halide salt-containing hydrophilic group is preferably a compound represented by the following Formula (3):

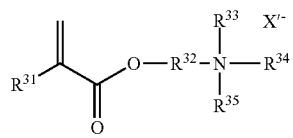

(3)

wherein $R^{31}$ represents a hydrogen atom or a linear or branched C1-C3 alkyl group; $R^{32}$ represents a linear or branched C1-C5 alkylene group; $R^{33}$ to $R^{35}$ are the same as or different from one another and each represent a hydrogen atom or a linear or branched C1-C5 alkyl group; and X' represents a halogen atom.

In Formula (3), examples of $R^{31}$ include those mentioned for $R^{11}$ in Formula (1), and preferred are those described for the preferred $R^{11}$ in Formula (1). Examples of $R^{32}$ include those mentioned for $R^{12}$ in Formula (1), and preferred are those described for the preferred $R^{12}$ in Formula (1).

In Formula (3), $R^{33}$ to $R^{35}$ are the same as or different from one another and each are a hydrogen atom or a linear or branched C1-C5 alkyl group, preferably a linear or branched C1-C3 alkyl group, and more preferably a linear or branched C1-C2 alkyl group. Specific examples include a hydrogen atom, a methyl group, an ethyl group, a propyl group, an isopropyl group, and a butyl group. Preferred are a methyl group, an ethyl group, and a propyl group, and more preferred is a methyl group.

Examples of the compound represented by Formula (3) include 2-((meth)acryloyloxy)ethyl trimethylammonium chloride, ((meth)acryloyloxy)methyl trimethylammonium chloride, 2-((meth)acryloyloxy)ethyl triethylammonium chloride, 2-((meth)acryloyloxy)ethyl trimethylammonium bromide, ((meth)acryloyloxy)methyl trimethylammonium bromide, and 2-((meth)acryloyloxy)ethyl triethylammonium bromide. Preferred among these is 2-((meth)acryloyloxy)ethyl trimethylammonium chloride because the effect of the present invention can be better achieved.

Specifically, the polymerizable compound B containing a zwitterionic group is preferably a compound represented by the Formula (4) below, and is particularly suitably a compound represented by the Formula (5) below.

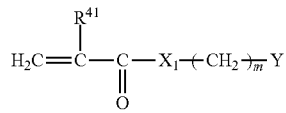

(4)

In Formula (4), $R^{41}$ represents —H or —CH$_3$; $X^1$ represents —O— or —NH—; m represents an integer of 1 or higher; and Y represents a zwitterionic group.

In Formula (4), $R^{41}$ is preferably —CH$_3$, $X^1$ is preferably —O—, and m is preferably an integer of 1 to 10. In the zwitterionic group designated by Y, the cation may be a quaternary ammonium such as tetraalkylammonium, and the anion may be a carboxylic acid, sulfonic acid, or phosphate.

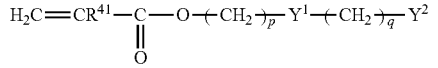

(5)

In Formula (5), $R^{41}$ represents —H or —$CH_3$; p and q each represent an integer of 1 or higher; and $Y^1$ and $Y^2$ represent ionic functional groups having charges opposite to each other.

In Formula (5), p is preferably an integer of 2 or higher, and more preferably an integer of 2 to 10, and q is preferably an integer of 1 to 10, and more preferably an integer of 2 to 4. Moreover, preferred examples of $R^{41}$ are the same as mentioned above. Examples of $Y^1$ and $Y^2$ are those mentioned for the cation and anion above.

Typical suitable examples of the polymerizable compound B containing a zwitterionic group include compounds represented by the following Formulae (5-1) to (5-4).

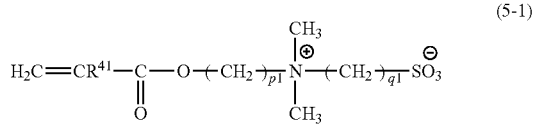
(5-1)

In Formula (5-1), $R^{41}$ represents a hydrogen atom or a methyl group, and p1 and q1 each represent an integer of 1 to 10.

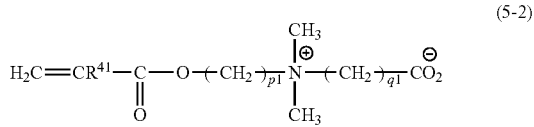
(5-2)

In Formula (5-2), $R^{41}$ represents a hydrogen atom or a methyl group, and p1 and q1 each represent an integer of 1 to 10.

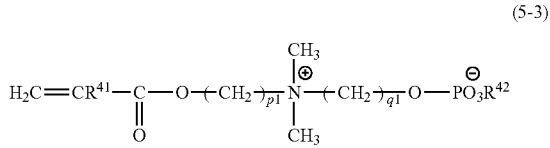
(5-3)

In Formula (5-3), $R^{41}$ represents a hydrogen atom or a methyl group; $R^{42}$ represents a C1-C6 hydrocarbon group; and p1 and q1 each represent an integer of 1 to 10.

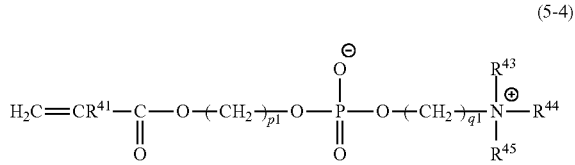
(5-4)

In Formula (5-4), $R^{41}$ represents a hydrogen atom or a methyl group; $R^{43}$, $R^{44}$, and $R^{45}$ are the same as or different from one another and each represent a C1 or C2 hydrocarbon group; and p1 and q1 each represent an integer of 1 to 10.

Examples of the compound represented by Formula (5-1) include dimethyl(3-sulfopropyl) (2-(meth)acryloyloxyethyl) ammonium betaine and dimethyl(3-sulfopropyl) (2-(meth) acryloyloxyethyl)ammonium hydroxide. Examples of the compound represented by Formula (5-2) include dimethyl (2-carboxyethyl) (2-(meth)acryloyloxyethyl)ammonium betaine. Examples of the compound represented by Formula (5-3) include dimethyl(3-methoxyphosphopropyl) (2-(meth) acryloyloxyethyl)ammonium betaine. Examples of the compound represented by Formula (5-4) include 2-(meth)acryloyloxyethyl phosphorylcholine. Preferred among these is dimethyl(3-sulfopropyl) (2-(meth)acryloyloxyethyl)ammonium hydroxide because the effect of the present invention can be better achieved.

For the copolymerization of the silane compound A and the polymerizable compound B, conventionally known polymerization methods may be used as appropriate. In exemplary methods, the silane compound A and the polymerizable compound B are dissolved in an organic solvent such as methanol and the atmosphere is then substituted with inert gas, followed by (i) irradiation with ultraviolet light in the presence of a photopolymerization initiator such as benzophenone, or by (ii) heating at 40 to 150° C. in the presence of a heat polymerization initiator such as azobisisobutyronitrile (AIBN) or benzoyl peroxide (BPO). In this manner, radical polymerization (photoradical polymerization, heat radical polymerization) is allowed to proceed to produce a copolymer C. The procedure for polymerization, temperature, pressure, irradiation dose, irradiation time, heating temperature, heating time, and the like are not particularly limited, and conventionally known conditions may be used.

The polymer e is obtained by copolymerizing a polymerizable compound a that is reactive with a silane compound d with a polymerizable compound b that contains a functional group to give a copolymer c, and further reacting the copolymer c with the silane compound d.

The polymerizable compound a may be, for example, a compound containing in the molecule at least one polymerizable group and a group reactive with the silane compound d. Examples of the polymerizable group include those mentioned for the silane compound A, and preferred are those described for the preferred silane compound A. The group reactive with the silane compound d is not particularly limited as long as it is a group capable of reacting, for example, addition reacting or condensation reacting, with any of various silane compounds. Examples include an epoxy group, an amino group, a (meth)acrylic group, and a vinyl group. Preferred among these is an epoxy group.

The polymerizable compound a is preferably, for example, a compound represented by the following Formula (6):

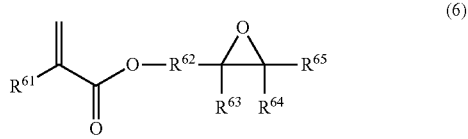
(6)

wherein $R^{61}$ represents a hydrogen atom or a linear or branched C1-C4 alkyl group; $R^{62}$ represents a linear or branched C1-C5 alkylene group or a linear or branched C1-C5 alkylene group containing an ether bond; and $R^{63}$ to $R^{65}$ are the same as or different from one another and each represent a hydrogen atom or a linear or branched C1-C3 alkyl group.

In Formula (6), examples of $R^{61}$ include those mentioned for $R^{11}$ in Formula (1), and preferred are those described for the preferred $R^{11}$ in Formula (1).

In Formula (6), examples of the linear or branched C1-C5 alkylene group for $R^{62}$ include those mentioned for $R^{12}$ in Formula (1). The linear or branched C1-C5 alkylene group containing an ether bond for $R^{62}$ may be any group having an ether bond bonded to any position of the alkylene group, such as, for example, a group represented by —$(CH_2)_{m1}$—O—$(CH_2)_{n1}$— wherein m1 is an integer of 0 to 5, n1 is an integer of 0 to 5, and m1+n1 is an integer of 1 to 5.

$R^{62}$ is preferably a linear or branched C1-C5 alkylene group, and more preferably a linear or branched C1-C3 alkylene group.

$R^{63}$ to $R^{65}$ are the same as or different from one another and each are a hydrogen atom or a linear or branched C1-C3 alkyl group, preferably a hydrogen atom or a linear or branched C1-C2 alkyl group, and more preferably a hydrogen atom. Specific examples include a hydrogen atom, a methyl group, an ethyl group, a propyl group, and an isopropyl group. Preferred are a hydrogen atom, a methyl group, and an ethyl group, and more preferred is a hydrogen atom.

Examples of the compound represented by Formula (6) include glycidyl(meth)acrylate and 4-hydroxybutyl(meth)acrylate glycidyl ether. Preferred among these is glycidyl (meth)acrylate because the effect of the present invention can be better achieved.

Examples of the polymerizable compound b that contains a functional group include those mentioned for the polymerizable compound B, and preferred are those described for the preferred polymerizable compound B.

For the copolymerization of the polymerizable compound a and the polymerizable compound b, the same methods as described for the copolymerization of the silane compound A and the polymerizable compound B may be used as appropriate.

The silane compound d may be, for example, any of various silane compounds containing a group capable of reacting (e.g., addition reacting or condensation reacting) with the polymerizable compound a. The group capable of reacting with the polymerizable compound a is not particularly limited as long as it is a group capable of reacting, for example, addition reacting or condensation reacting, with the polymerizable compound a. Examples include an amino group, a thiol group, and an epoxy group. Preferred among these is an amino group.

The silane compound d may suitably be a compound represented by the following Formula (7):

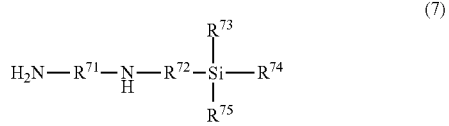

(7)

wherein $R^{71}$ and $R^{72}$ are the same as or different from each other and each represent a linear or branched C1-C5 alkylene group, and $R^{73}$ to $R^{75}$ are the same as or different from one another and each represent a halogen atom, a hydroxy group, a linear or branched C1-C3 alkyl group, or a linear or branched C1-C3 alkoxy group, provided that at least one of $R^{73}$ to $R^{75}$ is a halogen atom, a hydroxy group, or a linear or branched C1-C3 alkoxy group.

In Formula (7), examples of $R^{71}$ and $R^{72}$ include those mentioned for $R^{12}$ in Formula (1), and preferred are those described for the preferred $R^{12}$ in Formula (1). $R^{73}$ to $R^{75}$ may be the same as or different from one another, and examples thereof include those mentioned for $R^{13}$ to $R^{15}$ in Formula (1), and preferably those described for the preferred $R^{13}$ to $R^{15}$ in Formula (1).

Examples of the compound represented by Formula (7) include N-(2-aminoethyl)-3-aminopropyltrimethoxysilane, and N-(2-aminoethyl)-3-aminopropyltriethoxysilane. Preferred among these is N-(2-aminoethyl)-3-aminopropyltrimethoxysilane. In this case, the effect of the present invention can be better achieved.

For the reaction of the copolymer c and the silane compound d, conventionally known methods may be used as appropriate. In exemplary methods, the copolymer c and the silane compound d are dissolved in an organic solvent such as methanol and then reacted with stirring. In this manner, the reaction such as addition or condensation reaction is allowed to proceed to produce a polymer e. The temperature, pressure, reaction time, and the like are not particularly limited, and conventionally known conditions may be used.

Examples of metal medical devices that may be used in the present invention include guide wires, stents, needles, stylets, and metal tubes. Especially in the case of guide wires, the effects of imparting lubricity, of improving the durability of the lubricant layer on the surface, and of preventing deterioration of sliding properties work most effectively, so that the insertability, push ability, and sliding properties into/in the body cavity or tissue, and the durability of these properties are improved. Consequently, the effect of the present invention is particularly remarkably exerted in this case. Thus, in another suitable embodiment of the present invention, the metal medical device of the present invention is a guide wire. Especially in the case of stents, on the other hand, the effects of imparting low protein adsorption and low cell adsorption properties, of improving the durability of the lubricant layer on the surface, and of preventing deterioration of low protein adsorption and low cell adsorption properties work most effectively, so that the lubricant layer is prevented from being washed away and removed during the long indwelling time, and the effect of preventing adhesion of proteins and cells to the stent surface is maintained. Consequently, the effect of the present invention is particularly remarkably exerted in this case. Thus, in still another suitable embodiment of the present invention, the metal medical device of the present invention is a stent.

Exemplary materials of the metal medical devices of the present invention include metals such as stainless steel, nickel-titanium alloy, iron, titanium, aluminum, tin, and zinc-tungsten alloy. Among these, stainless steel and nickel-titanium alloy are preferred in view of bonding between the surface of the metal medical device and the lubricant layer. Thus, in another suitable embodiment of the present invention, the metal medical device of the present invention includes a core wire made of stainless steel or nickel-titanium alloy.

The metal medical devices of the present invention can be prepared, for example, by treating the surface of a metal medical device with the copolymer C or polymer e. The treatment of the surface of a metal medical device with the copolymer C or polymer e causes hydrolysis of the copolymer C or polymer e, a dehydration/deoxygenation condensation reaction between the copolymer C or polymer e and hydroxy groups present on the surface of the metal medical device, and the like, whereby the hydroxy groups on the surface of the metal medical device and the copolymer C or polymer e are bonded to each other through a chemical bond. Therefore, lubricity, low protein adsorption properties and low cell adsorption properties are imparted to the surface of the metal medical device. Moreover, the durability of the lubricant layer on the surface is improved to prevent deterioration of the sliding properties, low protein adsorption properties and low cell adsorption properties of the metal medical device.

Thus, the metal medical devices of the present invention may be prepared, for example, by a method including the step of treating the surface of a metal medical device with the copolymer C or polymer e.

The metal medical devices of the present invention have a surface treated with the copolymer C or polymer e at least at a portion where lubricity, low protein adsorption properties and low cell adsorption properties are required. The entire surface of the metal medical devices may be treated with the copolymer C or polymer e.

For the treatment of the surface of a metal medical device with the copolymer C or polymer e, for example, a solution prepared by mixing the copolymer C or polymer e with a solvent may be applied or sprayed to the metal medical device. Alternatively, the metal medical device may be immersed in the solution. The application, spraying, and immersion may be carried out by commonly employed methods.

The solvent used in the preparation of the solution may be a solvent commonly used in these treatments, and examples include water, perfluorohexane, acidic water, methanol, ethanol, and a mixture of water and methanol or ethanol. In particular, in the case where the copolymer C or polymer e contains a polyoxyalkylene group, a metal salt-containing hydrophilic group, a halide salt-containing hydrophilic group, or a zwitterionic group, suitable are water, acidic water, methanol, ethanol, and a mixture of water and methanol or ethanol. In the case where the copolymer C or polymer e contains a fluorine-containing hydrophobic group, suitable is perfluorohexane.

The concentration of the solution may be determined as appropriate depending on the method of treatment with the copolymer C or polymer e, the kind of solution used for the treatment, and the like.

The solution preferably has a pH of 5 or lower. When the solution of the copolymer C or polymer e used for treatment of the surface of a metal medical device has a pH of 5 or lower, hydrolysis is promoted so that a stronger chemical bond can be formed between hydroxy groups present on the surface of the metal medical device and the copolymer C or polymer e. The pH is more preferably 4 or lower. The pH is also preferably 1 or higher, and more preferably 2 or higher.

The pH may be adjusted by any method, including conventionally known methods such as addition of an acid or alkali. Exemplary acids usable for the pH adjustment include inorganic acids such as sulfuric acid, nitric acid, and hydrochloric acid, and organic acids such as acetic acid. Exemplary alkalis include ammonia water, sodium hydroxide, and potassium hydroxide.

In the preparation method, a metal medical device may optionally be washed with acetone, ethanol, or the like and then dried prior to the treatment step described above. The drying time and drying temperature may be set as appropriate within conventional ranges.

In the preparation method, the surface-treated metal medical device obtained after the treatment step may optionally be washed with water, acetone, ethanol, or the like and then dried. The drying time and drying temperature may be set as appropriate within conventional ranges.

The preparation method preferably includes the step of holding the surface-treated metal medical device obtained in the treatment step, at a humidity of 50% or higher. By holding the metal medical device surface-treated with the copolymer C or polymer e at a humidity of 50% or higher, hydrolysis of the copolymer C or polymer e, a dehydration/deoxygenation condensation reaction between the copolymer C or polymer e and hydroxy groups present on the surface of the metal medical device, and the like are further promoted so that the chemical bond formed between hydroxy groups present on the surface of the metal medical device and the copolymer C or polymer e becomes stronger. Therefore, the durability of the lubricant layer on the surface of the metal medical device is further improved to further prevent deterioration of the sliding properties, low protein adsorption properties and low cell adsorption properties of the metal medical device of the present invention. The humidity at which the surface-treated metal medical device is held is more preferably 60% or higher, and still more preferably 80% or higher. The upper limit is not particularly limited, and is preferably 100%, for example.

In the holding step, the time and temperature for holding the metal medical device at a humidity of 50% or higher may be appropriately determined so that the chemical bond formed between hydroxy groups present on the surface of the metal medical device and the copolymer C or polymer e becomes stronger to further prevent deterioration of the sliding properties, low protein adsorption properties and low cell adsorption properties of the metal medical device of the present invention. For example, the holding time is preferably 0.5 to 60 hours and the holding temperature is preferably 20 to 60° C.

EXAMPLES

The present invention is more specifically described by reference to examples below, but is not limited only to these examples.

Example 1

An amount of 0.082 g of 3-acryloxypropyltrimethoxysilane, 0.86 g of 3-sulfopropyl methacrylate potassium salt (SPMK), and 0.2 mg of benzophenone were dissolved in 10 ml of methanol. A glass vessel was charged with the resulting solution and covered with a lid. The vessel was purged with argon for 30 minutes, and the solution was then irradiated with LED-UV having a wavelength of 365 nm for 90 minutes. In this manner, a polymer was prepared, recovered and dried.

A SUS guide wire (core wire) was washed with acetone and then dried. The recovered polymer was dissolved in water (5 wt % aqueous solution). The washed guide wire was immersed in the aqueous solution and then pulled out. The resulting guide wire was left at high humidity (humidity of 90%) for 24 hours for reaction. Then, the guide wire was washed with water and dried to prepare a surface-treated guide wire.

Example 2

A surface-treated guide wire was prepared in the same manner as in Example 1, except that 2-(methacryloyloxy)ethyl trimethylammonium chloride (MTAC) was used instead of SPMK.

Example 3

A surface-treated guide wire was prepared in the same manner as in Example 1, except that [2-(methacryloyloxy)ethyl]dimethyl-(3-sulfopropyl)ammonium hydroxide was used instead of SPMK.

Example 4

A surface-treated guide wire was prepared in the same manner as in Example 1, except that 3-methacryloxypropyltrimethoxysilane was used instead of 3-acryloxypropyltrimethoxysilane.

Example 5

A surface-treated guide wire was prepared in the same manner as in Example 1, except that a nickel-titanium alloy guide wire was used instead of the SUS guide wire.

Example 6

A surface-treated guide wire was prepared in the same manner as in Example 1, except that the recovered polymer was prepared into a 5 wt % acetic acid aqueous solution (pH 3), and the washed guide wire was immersed in this aqueous solution and then pulled out and left at high humidity (humidity of 90%) for one hour for reaction.

Example 7

An amount of 0.082 g of glycidyl methacrylate, 0.86 g of SPMK, and 0.2 mg of benzophenone were dissolved in 10 ml of ethanol. A glass vessel was charged with the resulting solution and covered with a lid. The vessel was purged with argon for 30 minutes, and the solution was then irradiated with LED-UV having a wavelength of 365 nm for 90 minutes. In this manner, a polymer was prepared, recovered and dried.

An amount of 0.42 g of the recovered polymer was dissolved in 10 ml of methanol, and 0.02 g of N-(2-aminoethyl)-3-aminopropyltrimethoxysilane was added thereto. The mixture was reacted with stirring at 40° C. for 24 hours. The resulting product was recovered and dried.

A SUS guide wire (core wire) was washed with acetone and then dried. The recovered product was dissolved in water (5 wt % aqueous solution). The washed guide wire was immersed in the aqueous solution and then pulled out. The resulting guide wire was left at high humidity (humidity of 90%) for 24 hours for reaction. Then, the guide wire was washed with water and dried to prepare a surface-treated guide wire.

Example 8

A surface-treated guide wire was prepared in the same manner as in Example 7, except that MTAC was used instead of SPMK.

Example 9

A surface-treated guide wire was prepared in the same manner as in Example 7, except that [2-(methacryloyloxy)ethyl]dimethyl-(3-sulfopropyl)ammonium hydroxide was used instead of SPMK.

Example 10

A surface-treated guide wire was prepared in the same manner as in Example 7, except that the recovered product was prepared into a 5 wt % acetic acid aqueous solution (pH 3), and the washed guide wire was immersed in this aqueous solution and then pulled out and left at high humidity (90%) for one hour for reaction.

Comparative Example 1

After a SUS guide wire (core wire) was only washed with acetone and dried, the guide wire was directly subjected to the following evaluation of sliding properties.

Comparative Example 2

After a nickel-titanium alloy guide wire (core wire) was only washed with acetone and dried, the guide wire was directly subjected to the following evaluation of sliding properties.

<Evaluation of Sliding Properties>

Water was put on each surface-treated guide wire or guide wire and the guide wire was then rubbed by a hand to evaluate sliding properties.

As a result of the evaluation, the surface-treated guide wires of Examples 1 to 10 were found to have a slippery surface and improved sliding properties as compared to the guide wires of Comparative Examples 1 and 2. Moreover, rubbing 100 times gave no change in slipperiness.

<Low Protein Adsorption Properties, Low Cell Adsorption Properties>

Furthermore, it is known that polyoxyalkylene groups adsorb only a small amount of proteins and cells and that metal salt-containing hydrophilic groups, halide salt-containing hydrophilic groups, and zwitterionic groups adsorb a smaller amount of proteins and cells than polyoxyalkylene groups. Accordingly, the samples of the examples also adsorbed only a small amount of proteins and cells.

The invention claimed is:

1. A metal medical device, having a surface at least partially chemically bound to a copolymer C of a polymerizable silane compound A and a polymerizable compound B that contains a functional group, wherein the polymerizable compound B is at least one selected from the group consisting of a compound of Formula (2) and a compound of Formula (5-1):

$$R^{21}\!\!\diagup\!\!\diagdown\!\!\underset{O}{\overset{\|}{C}}\!\!-\!\!O\!-\!R^{22}\!-\!X \qquad (2)$$

wherein $R^{21}$ represents a hydrogen atom or a linear or branched C1-C3 alkyl group; $R^{22}$ represents a linear or branched C1-C5 alkylene group; and X represents a metal salt-containing hydrophilic group wherein the metal is an alkali metal or an alkaline earth metal, $$H_2C\!\!=\!\!CR^{41}\!-\!\underset{O}{\overset{\|}{C}}\!-\!O\!-\!\!\left(CH_2\right)_{\!p1}\!\!\overset{CH_3}{\underset{CH_3}{\overset{\oplus}{N}}}\!\!\left(CH_2\right)_{\!q1}\!\!-\!SO_3^{\ominus} \qquad (5\text{-}1)$$

wherein $R^{41}$ represents a hydrogen atom or a methyl group, and p1 and q1 each represent an integer of 1 to 10.

2. A metal medical device, having a surface at least partially chemically bound to a polymer (e), the polymer (e) being obtained by reacting a copolymer (c) with a silane compound (d), the copolymer (c) being formed from a polymerizable compound (a) that is reactive with the silane compound (d), and a polymerizable compound (b) that contains a functional group,
wherein the polymerizable compound (b) is at least one selected from the group consisting of a compound of Formula (2) and a compound of Formula (5-1):

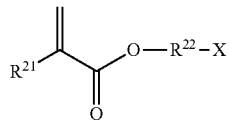
(2)

wherein $R^{21}$ represents a hydrogen atom or a linear or branched C1-C3 alkyl group; $R^{22}$ represents a linear or branched C1-C5 alkylene group; and X represents a metal salt-containing hydrophilic group wherein the metal is an alkali metal or an alkaline earth metal,

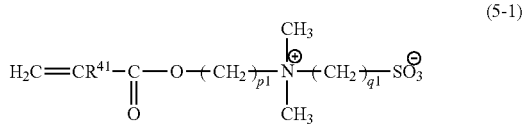
(5-1)

wherein $R^{41}$ represents a hydrogen atom or a methyl group, and p1 and q1 each represent an integer of 1 to 10.

3. The metal medical device according to claim 1, wherein polymerizable silane compound A is a compound of Formula (1):

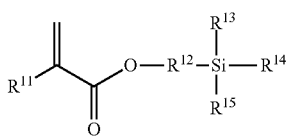
(1)

wherein $R^{11}$ represents a hydrogen atom or a linear or branched C1-C3 alkyl group; $R^{12}$ represents a linear or branched C1-C5 alkylene group; and $R^{13}$ to $R^{15}$ are the same as or different from one another and each represent a halogen atom, a hydroxy group, a linear or branched C1-C3 alkyl group, or a linear or branched C1-C3 alkoxy group, provided that at least one of $R^{13}$ to $R^{15}$ is a halogen atom, a hydroxy group, or a linear or branched C1-C3 alkoxy group.

4. The metal medical device according to claim 2, wherein polymerizable compound (a) is a compound of Formula (6):

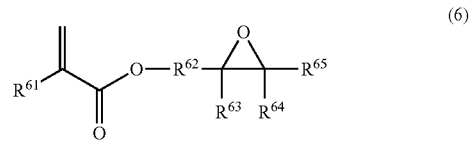
(6)

wherein $R^{61}$ represents a hydrogen atom or a linear or branched C1-C4 alkyl group; $R^{62}$ represents a linear or branched C1-C5 alkylene group or a linear or branched C1-C5 alkylene group containing an ether bond; and $R^{63}$ to $R^{65}$ are the same as or different from one another and each represent a hydrogen atom or a linear or branched C1-C3 alkyl group.

5. The metal medical device according to claim 2, wherein silane compound (d) is a compound of Formula (7):

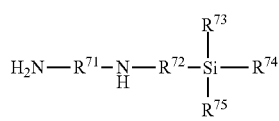
(7)

wherein $R^{71}$ and $R^{72}$ are the same as or different from each other and each represent a linear or branched C1-C5 alkylene group, and $R^{73}$ to $R^{75}$ are the same as or different from one another and each represent a halogen atom, a hydroxy group, a linear or branched C1-C3 alkyl group, or a linear or branched C1-C3 alkoxy group, provided that at least one of $R^{73}$ to $R^{75}$ is a halogen atom, a hydroxy group, or a linear or branched C1-C3 alkoxy group.

6. The metal medical device according to claim 4, wherein silane compound (d) is a compound of Formula (7):

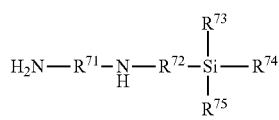
(7)

wherein $R^{71}$ and $R^{72}$ are the same as or different from each other and each represent a linear or branched C1-C5 alkylene group, and $R^{73}$ to $R^{75}$ are the same as or different from one another and each represent a halogen atom, a hydroxy group, a linear or branched C1-C3 alkyl group, or a linear or branched C1-C3 alkoxy group, provided that at least one of $R^{73}$ to $R^{75}$ is a halogen atom, a hydroxy group, or a linear or branched C1-C3 alkoxy group.

* * * * *